US012590336B2

(12) United States Patent
Bagchi et al.

(10) Patent No.: US 12,590,336 B2
(45) Date of Patent: Mar. 31, 2026

(54) ROLE OF PVT1 IN THE DIAGNOSIS AND TREATMENT OF MYC-DRIVEN CANCER

(71) Applicant: Sanford Burnham Prebys Medical Discovery Institute, La Jolla, CA (US)

(72) Inventors: Anindya Bagchi, San Diego, CA (US); Ashutosh Tiwari, San Diego, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 18/503,865

(22) Filed: Nov. 7, 2023

(65) Prior Publication Data

US 2024/0076749 A1    Mar. 7, 2024

Related U.S. Application Data

(62) Division of application No. 17/053,328, filed as application No. PCT/US2019/031349 on May 8, 2019, now Pat. No. 11,866,788.

(60) Provisional application No. 62/668,638, filed on May 8, 2018.

(51) Int. Cl.
*C12Q 1/6886*    (2018.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. |
| 4,373,071 A | 2/1983 | Itakura |
| 4,401,796 A | 8/1983 | Itakura |
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,973,679 A | 11/1990 | Caruthers et al. |
| 5,047,524 A | 9/1991 | Andrus et al. |
| 5,132,418 A | 7/1992 | Caruthers et al. |
| 5,153,319 A | 10/1992 | Caruthers et al. |
| 5,204,253 A | 4/1993 | Sanford et al. |
| 5,262,530 A | 11/1993 | Andrus et al. |
| 5,279,833 A | 1/1994 | Rose |
| 5,683,898 A | 11/1997 | Yazawa et al. |
| 5,700,642 A | 12/1997 | Monforte et al. |
| 11,866,788 B2 | 1/2024 | Bagchi et al. |
| 2004/0023267 A1 | 2/2004 | Morris |
| 2009/0098622 A1 | 4/2009 | Facciotti et al. |
| 2009/0311748 A1 | 12/2009 | Isogai et al. |
| 2013/0230547 A1 | 9/2013 | Sanda et al. |

| | | |
|---|---|---|
| 2018/0110788 A1 | 4/2018 | Toyoshima et al. |
| 2019/0117751 A1 | 4/2019 | Torigoe et al. |
| 2023/0058305 A1 | 2/2023 | Bagchi et al. |

FOREIGN PATENT DOCUMENTS

| | | |
|---|---|---|
| CN | 108220434 A | 6/2018 |
| CN | 106047880 B | 2/2019 |
| WO | WO-2019053003 A1 | 3/2019 |
| WO | WO-2019217572 A1 | 11/2019 |
| WO | WO-2021055846 A1 | 3/2021 |

OTHER PUBLICATIONS

Pleuvry et al (Receptors, agonists, and antagonists, Anaesthesia & Intensive Care Medicine, vol. 5, 2004, pp. 350-352) (Year: 2004).*
Hattab et al (Clinical Advances of siRNA-Based Nanotherapeutics for Cancer Treatment. Pharmaceutics. Jul. 2, 2021;13(7): 1009) (Year: 2021).*
Jia et al (Constructing the boundary between potent and ineffective siRNAs by MG-algorithm with C-features. BMC Bioinformatics. Aug. 13, 2022;23(1):337) (Year: 2022).*
Oh (siRNA delivery systems for cancer treatment; Advanced Drug Delivery Reviews 61 (2009) 850â86) (Year: 2009).*
Cavalli et al. Intertumoral Heterogeneity within Medulloblastoma Subgroups. Cancer Cell 31:737-754 (2017).
Felgner et al., Lipofection: A highly efficient, lipid-mediated DNA-transfection procedure, PNAS USA 84:7413-7414 (1987).
L'Abbate MYC-containing amplicons in acute myeloid leukemia: genomic structures, evolution, and transcriptional consequences. Leukemia 32(10):2152-2166 (2018).
Mannino et al. Liposome mediated gene transfer. BioTechniques 6(7):682-690 (1988).
PCT/US2019/031349 International Invitation to Pay Additional Fees dated Jul. 29, 2019.
PCT/US2019/031349 International Search Report and Written Opinion dated Oct. 16, 2019.
PCT/US2020/051626 International Search Report and Written Opinion dated Feb. 1, 2021.
Prive et al., Identification and characterization of three novel lipases belonging to families II and V from Anaerovibrio lipolyticus 5ST. PLoS One 8(8):e69076 [1-9] (2013).
Szoka et al., Comparative properties and methods of preparation of lipid vesicles (liposomes). Annual Review of Biophysics and Bioengineering 9:467-508 (1980).
Tashiro et al. MP99-18 Role of long non-coding RNA PVT1 in regulating MYC in human cancer. Journal of Urology 197(4S):e1327-e1328 (2017).
Tseng et al. PVT1 dependence in cancer with MYC copy-number increase. Nature 512(7512):82-86 (2014).
U.S. Appl. No. 17/053,328 Office Action dated Jan. 9, 2023.
U.S. Appl. No. 17/053,328 Office Action dated Jun. 7, 2023.

(Continued)

*Primary Examiner* — Zachariah Lucas
*Assistant Examiner* — Sarah A Alsomairy
(74) *Attorney, Agent, or Firm* — WILSON SONSINI GOODRICH & ROSATI

(57) ABSTRACT

Disclosed herein are methods of diagnosing and treating MYC-driven cancers by detecting a PVT1 splice variant in a biological sample from a subject.

8 Claims, No Drawings

Specification includes a Sequence Listing.

(56)          References Cited

OTHER PUBLICATIONS

Verduci et al. The oncogenic role of circPVT1 in head and neck squamous cell carcinoma is mediated through the mutant p53/YAP/TEAD transcription-competent complex. Genome Biol 18(1):237 (2017).

Xiao et al. Prognostic values of long noncoding RNA PVT1 in various carcinomas: An updated systematic review and meta-analysis. Cell Prolif 51(6):e12519 (2018).

Bagchi, Anindya. CSIG-32. MYC driven cancers are dependent on convergent oncogenic pathways induced by genomic rearrangements at PVT1. Neuro-oncology. 25(Suppl-5). V47. Abstract ID: NOAD179.0188 (2023).

Tiwari, Ashutosh et al. Synergistic RAS-MAPK and AKT activation in MYC driven tumors via adjacent PVT1 rearrangements. Biorxiv preprint. 70 pages (2025).

U.S. Appl. No. 17/760,724 Office Action dated Apr. 11, 2025.

* cited by examiner

SEQUENCE LISTING

```
Sequence total quantity: 95
SEQ ID NO: 1              moltype = DNA  length = 410
FEATURE                   Location/Qualifiers
source                    1..410
                          mol_type = unassigned DNA
                          organism = Homo sapiens
SEQUENCE: 1
gcctgatctt ttggccagaa ggagattaaa aagatgcccc tcaagatggc tgtgcctgtc   60
agctgcatgg agcttcgttc aagtattttc tgagcctgat ggatttacag tgatcttcag  120
tggtctgggg aataacgctg gtggaaccat gcactggaat gacacacgcc cggcacattt  180
caggatacta aaagtggttt taagggaggc tgtggctgaa tgcctcatgg attcttacag  240
cttggatgtc catgggggac gaaggactgc agctggctga gagggttgag atctctgttt  300
acttagatct ctgccaactt cctttgggtc tccctatgga atgtaagacc ccgactcttc  360
ctggtgaagc atctgatgca cgttccatcc ggcgctcagc tgggcttgag              410

SEQ ID NO: 2              moltype = DNA  length = 15
FEATURE                   Location/Qualifiers
misc_feature             1..15
                          note = Description of Artificial Sequence: Synthetic
                           oligonucleotide
source                    1..15
                          mol_type = other DNA
                          organism = synthetic construct
SEQUENCE: 2
ccatccggcg ctcag                                                     15

SEQ ID NO: 3              moltype = RNA  length = 21
FEATURE                   Location/Qualifiers
misc_feature             1..21
                          note = Description of Artificial Sequence: Synthetic
                           oligonucleotide
source                    1..21
                          mol_type = other RNA
                          organism = synthetic construct
SEQUENCE: 3
tgggcttgag gcctgatctt t                                              21

SEQ ID NO: 4              moltype = RNA  length = 21
FEATURE                   Location/Qualifiers
misc_feature             1..21
                          note = Description of Artificial Sequence: Synthetic
                           oligonucleotide
source                    1..21
                          mol_type = other RNA
                          organism = synthetic construct
SEQUENCE: 4
agatcaggcc tcaagcccat t                                              21

SEQ ID NO: 5              moltype = DNA  length = 19
FEATURE                   Location/Qualifiers
misc_feature             1..19
                          note = Description of Artificial Sequence: Synthetic
                           oligonucleotide
source                    1..19
                          mol_type = other DNA
                          organism = synthetic construct
SEQUENCE: 5
gccatcatga tggtacttt                                                 19

SEQ ID NO: 6              moltype = DNA  length = 21
FEATURE                   Location/Qualifiers
misc_feature             1..21
                          note = Description of Artificial Sequence: Synthetic
                           oligonucleotide
source                    1..21
                          mol_type = other DNA
                          organism = synthetic construct
misc_feature             1..19
                          note = RNA
misc_feature             20..21
                          note = DNA
SEQUENCE: 6
catcatgatg gtactttaat t                                              21

SEQ ID NO: 7              moltype = RNA  length = 21
FEATURE                   Location/Qualifiers
misc_feature             1..21
                          note = Description of Artificial Sequence: Synthetic
```

```
                            oligonucleotide
source                      1..21
                            mol_type = other RNA
                            organism = synthetic construct
SEQUENCE: 7
ttaaagtacc atcatgatgg c                                          21

SEQ ID NO: 8               moltype = DNA  length = 21
FEATURE                    Location/Qualifiers
misc_feature               1..21
                            note = Description of Artificial Sequence: Synthetic
                            oligonucleotide
source                      1..21
                            mol_type = other DNA
                            organism = synthetic construct
SEQUENCE: 8
ccggcacatt tcaggatact a                                          21

SEQ ID NO: 9               moltype = DNA  length = 21
FEATURE                    Location/Qualifiers
misc_feature               1..21
                            note = Description of Artificial Sequence: Synthetic
                            oligonucleotide
source                      1..21
                            mol_type = other DNA
                            organism = synthetic construct
misc_feature               1..19
                            note = RNA
misc_feature               20..21
                            note = DNA
SEQUENCE: 9
ggcacatttc aggatactat t                                          21

SEQ ID NO: 10              moltype = RNA  length = 20
FEATURE                    Location/Qualifiers
misc_feature               1..20
                            note = Description of Artificial Sequence: Synthetic
                            oligonucleotide
source                      1..20
                            mol_type = other RNA
                            organism = synthetic construct
SEQUENCE: 10
tagtatcctg amtgtgccgg                                            20

SEQ ID NO: 11              moltype = DNA  length = 315
FEATURE                    Location/Qualifiers
source                      1..315
                            mol_type = unassigned DNA
                            organism = Homo sapiens
SEQUENCE: 11
atgcacgttc catccggcgc tcagctgggc ttgaggcctg atcttttggc cagaaggaga  60
ttaaaaagat gcccctcaag atggctgtgc ctgtcagctg catggagctt cgttcaagta  120
ttttctgagc ctgatggatt tacagtgatc ttcagtggtc tggggaataa cgctggtgga  180
accatgcact ggaatgacac acgcccggca catttcagga tactaaaagt ggttttaagg  240
gaggctgtgg ctgaatgcct catggattct tacagcttgg atgtccatgg gggacgaagg  300
actgcagctg gctga                                                 315

SEQ ID NO: 12              moltype = AA  length = 104
FEATURE                    Location/Qualifiers
source                      1..104
                            mol_type = protein
                            organism = Homo sapiens
SEQUENCE: 12
MHVPSGAQLG LRPDLLARRR LKRCPSRWLC LSAAWSFVQV FSEPDGFTVI FSGLGNNAGG  60
TMHWNDTRPA HFRILKVVLR EAVAECLMDS YSLDVHGGRR TAAG                  104

SEQ ID NO: 13              moltype = DNA  length = 315
FEATURE                    Location/Qualifiers
source                      1..315
                            mol_type = unassigned DNA
                            organism = Homo sapiens
SEQUENCE: 13
atgcacgttc catccggcgc tcagctgggc ttgaggcctg atcttttggc cagaaggaga  60
ttaaaaagat gcccctcaag atggctgtgc ctgtcagctg catggagctt cgttcaagta  120
ttttctgagc ctgatggatt tacagtgatc ttcagtggtc tggggaataa cgctggtgga  180
accatgcact ggaatgacac acgcccggca catttcagga tactaaaagt ggttttaagg  240
gaggctgtgg ctgaatgcct catggattct tacagcttgg atgtccatgg gggacgaagg  300
actgcagctg gctga                                                 315
```

-continued

```
SEQ ID NO: 14               moltype = AA   length = 104
FEATURE                     Location/Qualifiers
source                      1..104
                            mol_type = protein
                            organism = Homo sapiens
SEQUENCE: 14
MHVPSGAQLG LRPDLLARRR LKRCPSRWLC LSAAWSFVQV FSEPDGFTVI FSGLGNNAGG   60
TMHWNDTRPA HFRILKVVLR EAVAECLMDS YSLDVHGGRR TAAG                    104

SEQ ID NO: 15               moltype = DNA   length = 315
FEATURE                     Location/Qualifiers
misc_feature                1..315
                            note = Description of Artificial Sequence: Synthetic
                             polynucleotide
source                      1..315
                            mol_type = other DNA
                            organism = synthetic construct
SEQUENCE: 15
atgcatgtac cttccggcgc ccaactcggc ctcagaccgg acctgttggc ccgacgacga   60
ctgaagcgat gccctagcag gtggctctgt ctgtcagctg cgtggtcttt tgtccaagtt   120
ttctccgagc cagatggttt cacagttatt ttctccgggt tgggtaacaa tgcgggcggc   180
actatgcatt ggaatgatac tagaccagca cactttagga tcttgaaagt ggtcctcagg   240
gaagcggtgg cggaatgtct gatggatagt tattcactgg acgtacatgg gggtcgccga   300
acagccgcag gctga                                                    315

SEQ ID NO: 16               moltype = DNA   length = 315
FEATURE                     Location/Qualifiers
misc_feature                1..315
                            note = Description of Artificial Sequence: Synthetic
                             polynucleotide
source                      1..315
                            mol_type = other DNA
                            organism = synthetic construct
SEQUENCE: 16
tgacacgttc catccggcgc tcagctgggc ttgaggcctg atcttttggc cagaaggaga   60
ttaaaaagat gccctcaag atggctgtgc ctgtcagctg catggagctt cgttcaagta   120
ttttctgagc ctgatggatt tacagtgatc ttcagtggtc tggggaataa cgctggtgga   180
acctgacact ggaatgacac acgcccggca catttcagga tactaaaagt ggttttaagg   240
gaggctgtgg ctgaatgcct ctgagattct tacagcttgg atgtccatgg gggacgaagg   300
actgcagctg gctga                                                    315

SEQ ID NO: 17               moltype = DNA   length = 48
FEATURE                     Location/Qualifiers
misc_feature                1..48
                            note = Description of Artificial Sequence: Synthetic
                             oligonucleotide
source                      1..48
                            mol_type = other DNA
                            organism = synthetic construct
SEQUENCE: 17
cggcgctcag ctgggcttga ggcctgatct tttggccaga aggagatt               48

SEQ ID NO: 18               moltype = DNA   length = 387
FEATURE                     Location/Qualifiers
source                      1..387
                            mol_type = unassigned DNA
                            organism = Homo sapiens
SEQUENCE: 18
gcctgatctt ttggccagaa ggagattaaa aagatgcccc tcaagatggc tgtgcctgtc   60
agctgcatgg agcttcgttc aagtattttc tgagcctgat ggatttacag tgatcttcag   120
tggtctgggg ataaacgctg gtggaaccat gcactggaat gacacacgcc cggcacattt   180
caggatacta aaagtggttt taagggaggc tgtggctgaa tgcctcatgg attcttacag   240
cttggatgtc catgggggac gaaggactgc agctggctga gagggttgag atctctgttt   300
acttagatct ctgccaactt cctttgggtc tccctatgga atgtaagacc ccgactcttc   360
ctggtgaagc atctgatgca cgttcca                                       387

SEQ ID NO: 19               moltype = DNA   length = 344
FEATURE                     Location/Qualifiers
source                      1..344
                            mol_type = unassigned DNA
                            organism = Homo sapiens
SEQUENCE: 19
gcctgatctt ttggccagaa ggagattaaa aagatgcccc tcaagatggc tgtgcctgtc   60
agctgcatgg agcttcgttc aagtattttc tgagcctgat ggatttacag tgatcttcag   120
tggtctgggg ataaacgctg gtggaaccat gcactggaat gacacacgcc cggcacattt   180
caggatacta aaagtggttt taagggaggc tgtggctgaa tgcctcatgg attcttacag   240
cttggatgtc catgggggac gaaggactgc agctggctga gagggttgag atctctgttt   300
acttagatct ctgccaactt cctttgggtc tccctatgga atgt                    344
```

```
SEQ ID NO: 20              moltype = DNA   length = 372
FEATURE                    Location/Qualifiers
source                     1..372
                           mol_type = unassigned DNA
                           organism = Homo sapiens
SEQUENCE: 20
gcctgatctt ttggccagaa ggagattaaa aagatgcccc tcaagatggc tgtgcctgtc    60
agctgcatgg agcttcgttc aagtattttc tgagcctgat ggatttacag tgatcttcag   120
tggtctgggg aataacgctg gtggaaccat gcactggaat gacacacgcc cggcacattt   180
caggatacta aaagtggttt taagggaggc tgtggctgaa tgcctcatgg attcttacag   240
cttggatgtc catgggggac gaaggactgc agctggctga gagggttgag atctctgttt   300
acttagatct ctgccaactt cctttgggtc tccctatgga atgtaagacc ccgactcttc   360
ctggtgaagc at                                                       372

SEQ ID NO: 21              moltype = DNA   length = 153
FEATURE                    Location/Qualifiers
source                     1..153
                           mol_type = unassigned DNA
                           organism = Homo sapiens
SEQUENCE: 21
gcctgatctt ttggccagaa ggagattaaa aagatgcccc tcaagatggc tgtgcctgtc    60
agctgcatgg agcttcgttc aagtattttc tgagcctgat ggatttacag tgatcttcag   120
tggtctgggg aataacgctg gtggaaccat gca                                153

SEQ ID NO: 22              moltype = DNA   length = 410
FEATURE                    Location/Qualifiers
source                     1..410
                           mol_type = unassigned DNA
                           organism = Homo sapiens
SEQUENCE: 22
gcctgatctt ttggccagaa ggagattaaa aagatgcccc tcaagatggc tgtgcctgtc    60
agctgcatgg agcttcgttc aagtattttc tgagcctgat ggatttacag tgatcttcag   120
tggtctgggg aataacgctg gtggaaccat gcactggaat gacacacgcc cggcacattt   180
caggatacta aaagtggttt taagggaggc tgtggctgaa tgcctcatgg attcttacag   240
cttggatgtc catgggggac gaaggactgc agctggctga gagggttgag atctctgttt   300
acttagatct ctgccaactt cctttgggtc tccctatgga atgtaagacc ccgactcttc   360
ctggtgaagc atctgatgca cgttccatcc ggcgctcagc tgggcttgag                410

SEQ ID NO: 23              moltype = DNA   length = 207
FEATURE                    Location/Qualifiers
source                     1..207
                           mol_type = unassigned DNA
                           organism = Homo sapiens
SEQUENCE: 23
gcctgatctt ttggccagaa ggagattaaa aagatgcccc tcaagatggc tgtgcctgtc    60
agctgcatgg agcttcgttc aagtattttc tgagcctgat ggatttacag tgatcttcag   120
tggtctgggg aataacgctg gtggaaccat gcactggaat gacacacgcc cggcacattt   180
caggatacta aaagtggttt taaggga                                       207

SEQ ID NO: 24              moltype = DNA   length = 395
FEATURE                    Location/Qualifiers
source                     1..395
                           mol_type = unassigned DNA
                           organism = Homo sapiens
SEQUENCE: 24
gcctgatctt ttggccagaa ggagattaaa aagatgcccc tcaagatggc tgtgcctgtc    60
agctgcatgg agcttcgttc aagtattttc tgagcctgat ggatttacag tgatcttcag   120
tggtctgggg aataacgctg gtggaaccat gcactggaat gacacacgcc cggcacattt   180
caggatacta aaagtggttt taagggaggc tgtggctgaa tgcctcatgg attcttacag   240
cttggatgtc catgggggac gaaggactgc agctggctga gagggttgag atctctgttt   300
acttagatct ctgccaactt cctttgggtc tccctatgga atgtaagacc ccgactcttc   360
ctggtgaagc atctgatgca cgttccatcc ggcgc                               395

SEQ ID NO: 25              moltype = DNA   length = 364
FEATURE                    Location/Qualifiers
source                     1..364
                           mol_type = unassigned DNA
                           organism = Homo sapiens
SEQUENCE: 25
gcctgatctt ttggccagaa ggagattaaa aagatgcccc tcaagatggc tgtgcctgtc    60
agctgcatgg agcttcgttc aagtattttc tgagcctgat ggatttacag tgatcttcag   120
tggtctgggg aataacgctg gtggaaccat gcactggaat gacacacgcc cggcacattt   180
caggatacta aaagtggttt taagggaggc tgtggctgaa tgcctcatgg attcttacag   240
cttggatgtc catgggggac gaaggactgc agctggctga gagggttgag atctctgttt   300
acttagatct ctgccaactt cctttgggtc tccctatgga atgtaagacc ccgactcttc   360
ctgg                                                                 364

SEQ ID NO: 26              moltype = DNA   length = 371
FEATURE                    Location/Qualifiers
```

-continued

```
source                  1..371
                        mol_type = unassigned DNA
                        organism = Homo sapiens
SEQUENCE: 26
ctcaagatgg ctgtgcctgt cagctgcatg gagcttcgtt caagtatttt ctgagcctga    60
tggatttaca gtgatcttca gtggtctggg gaataacgct ggtggaacca tgcactggaa   120
tgacacacgc ccggcacatt tcaggatact aaaagtggtt ttaagggagg ctgtggctga   180
atgcctcatg gattcttaca gcttggatgt ccatgggg ga cgaaggactg cagctggctg   240
agagggttga gatctctgtt tacttagatc tctgccaact tcctttgggt ctccctatgg   300
aatgtaagac cccgactctt cctggtgaag catctgatgc acgttccatc cggcgctcag   360
ctgggcttga g                                                        371

SEQ ID NO: 27           moltype = DNA   length = 129
FEATURE                 Location/Qualifiers
source                  1..129
                        mol_type = unassigned DNA
                        organism = Homo sapiens
SEQUENCE: 27
agggttgaga tctctgttta cttagatctc tgccaacttc ctttgggtct ccctatggaa    60
tgtaagaccc cgactcttcc tggtgaagca tctgatgcac gttccatccg gcgctcagct   120
gggcttgag                                                           129

SEQ ID NO: 28           moltype = DNA   length = 322
FEATURE                 Location/Qualifiers
source                  1..322
                        mol_type = unassigned DNA
                        organism = Homo sapiens
SEQUENCE: 28
tctgagcctg atggatttac agtgatcttc agtggtctgg ggaataacgc tggtggaacc    60
atgcactgga atgacacacg cccggcacat ttcaggatac taaaagtggt tttaagggag   120
gctgtggctg aatgcctcat ggattcttac agcttggatg tccatggggg acgaaggact   180
gcagctggct gagagggttg agatctctgt ttacttagat ctctgccaac ttcctttggg   240
tctccctatg gaatgtaaga ccccgactct tcctggtgaa gcatctgatg cacgttccat   300
ccggcgctca gctgggcttg ag                                            322

SEQ ID NO: 29           moltype = DNA   length = 353
FEATURE                 Location/Qualifiers
source                  1..353
                        mol_type = unassigned DNA
                        organism = Homo sapiens
SEQUENCE: 29
gtcagctgca tggagcttcg ttcaagtatt ttctgagcct gatggattta cagtgatctt    60
cagtgctctg gggaataacg ctggtggaac catgcactgg aatgacacac gcccggcaca   120
tttcaggata ctaaaagtgg ttttaaggga ggctgtggct gaatgcctca tggattctta   180
cagcttggat gtccatgggg gacgaaggac tgcagctggc tgagagggtt gagatctctg   240
tttacttaga tctctgccaa cttcctttgg gtctccctat ggaatgtaag accccgactc   300
ttcctggtga agcatctgat gcacgttcca tccggcgctc agctgggctt gag          353

SEQ ID NO: 30           moltype = DNA   length = 10
FEATURE                 Location/Qualifiers
source                  1..10
                        mol_type = unassigned DNA
                        organism = Homo sapiens
SEQUENCE: 30
cctgatcttt                                                           10

SEQ ID NO: 31           moltype = DNA   length = 10
FEATURE                 Location/Qualifiers
source                  1..10
                        mol_type = unassigned DNA
                        organism = Homo sapiens
SEQUENCE: 31
gggcttgagg                                                           10

SEQ ID NO: 32           moltype = DNA   length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 32
gctgggcttg aggcctgatc ttttg                                          25

SEQ ID NO: 33           moltype = AA   length = 104
FEATURE                 Location/Qualifiers
source                  1..104
                        mol_type = protein
```

```
                         organism = Homo sapiens
SEQUENCE: 33
MHVPSGAQLG LRPDLLARRR LKRCPSRWLC LSAAWSFVQV FSEPDGFTVI FSGLGNNAGG    60
TMHWNDTRPA HFRILKVVLR EAVAECLMDS YSLDVHGGRR TAAG                     104

SEQ ID NO: 34            moltype = AA  length = 149
FEATURE                  Location/Qualifiers
source                   1..149
                         mol_type = protein
                         organism = Homo sapiens
SEQUENCE: 34
MGPRAGRARG GRDEEGRRRA ASKDVPRDPR HLPVDFLAER MLAVPVTCGD TARSALQPDL    60
LARRRLKRCP SRWLCLSAAW SFVQVFSEPD GFTVIFSGLG NNAGGTMHWN DTRPAHFRIL    120
KVVLREAVAE CLMDSYSLDV HGGRRTAAG                                      149

SEQ ID NO: 35            moltype = DNA  length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 35
cctgtgacct gtggagacac                                               20

SEQ ID NO: 36            moltype = DNA  length = 140
FEATURE                  Location/Qualifiers
source                   1..140
                         mol_type = unassigned DNA
                         organism = Homo sapiens
SEQUENCE: 36
cttgcggaaa ggatgttggc ggtccctgtg acctgtggag acacggccag atctgccctc    60
cagcctgatc ttttggccag aaggagatta aaaagatgcc cctcaagatg gctgtgcctg    120
tcagctgcat ggagcttcgt                                               140

SEQ ID NO: 37            moltype = DNA  length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 37
gccatcttga ggggcatctt                                               20

SEQ ID NO: 38            moltype = DNA  length = 165
FEATURE                  Location/Qualifiers
misc_feature             1..165
                         note = Description of Artificial Sequence: Synthetic
                          polynucleotide
source                   1..165
                         mol_type = other DNA
                         organism = synthetic construct
SEQUENCE: 38
aatacgactc actatagggc gaattgaatt tagcggccgc gaattcgccc ttcctgtgac    60
ctgtggagac acggccagat ctgccctcca gcctgatctt ttggccagaa ggagattaaa    120
aagatgcccc tcaagatggc aagggcgaat tcgtttaaac ctgca                   165

SEQ ID NO: 39            moltype = DNA  length = 140
FEATURE                  Location/Qualifiers
misc_feature             1..140
                         note = Description of Artificial Sequence: Synthetic
                          polynucleotide
source                   1..140
                         mol_type = other DNA
                         organism = synthetic construct
SEQUENCE: 39
aatacgactc actatagggc gaattgaatt tagcggccgc gaattcgccc ttcctgtgac    60
ctgtggagac acggccagat ctgccctcca gcctgatctt ttggccagaa ggagattaaa    120
aagatgcccc tcaagatggc                                               140

SEQ ID NO: 40            moltype = DNA  length = 140
FEATURE                  Location/Qualifiers
misc_feature             1..140
                         note = Description of Artificial Sequence: Synthetic
                          polynucleotide
source                   1..140
                         mol_type = other DNA
                         organism = synthetic construct
```

```
SEQUENCE: 40
aatacgactc actatagggc gaattgaatt tagcggccgc gaattcgccc ttcctgtgac   60
ctgtggagac acggccagat ctgccctcca gcctgatctt ttggccagaa ggagattaaa  120
aagatgcccc tcaagatggc                                               140

SEQ ID NO: 41              moltype = DNA   length = 165
FEATURE                    Location/Qualifiers
misc_feature               1..165
                           note = Description of Artificial Sequence: Synthetic
                            polynucleotide
source                     1..165
                           mol_type = other DNA
                           organism = synthetic construct
SEQUENCE: 41
aatacgactc actatagggc gaattgaatt tagcggccgc gaattcgccc ttcctgtgac   60
ctgtggagac acggccagat ctgccctcca gcctgatctt ttggccagaa ggagattaaa  120
aagatgcccc tcaagatggc aagggcgaat tcgtttaaac ctgca                  165

SEQ ID NO: 42              moltype = DNA   length = 140
FEATURE                    Location/Qualifiers
misc_feature               1..140
                           note = Description of Artificial Sequence: Synthetic
                            polynucleotide
source                     1..140
                           mol_type = other DNA
                           organism = synthetic construct
SEQUENCE: 42
aatacgactc actatagggc gaattgaatt tagcggccgc gaattcgccc ttcctgtgac   60
ctgtggagac acggccagat ctgccctcca gcctgatctt ttggccagaa ggagattaaa  120
aagatgcccc tcaagatggc                                               140

SEQ ID NO: 43              moltype = DNA   length = 18
FEATURE                    Location/Qualifiers
misc_feature               1..18
                           note = Description of Artificial Sequence: Synthetic
                            oligonucleotide
source                     1..18
                           mol_type = other DNA
                           organism = synthetic construct
SEQUENCE: 43
aatacgactc actatagg                                                 18

SEQ ID NO: 44              moltype = DNA   length = 165
FEATURE                    Location/Qualifiers
misc_feature               1..165
                           note = Description of Artificial Sequence: Synthetic
                            polynucleotide
source                     1..165
                           mol_type = other DNA
                           organism = synthetic construct
SEQUENCE: 44
aatacgactc actatagggc gaattgaatt tagcggccgc gaattcgccc ttcctgtgac   60
ctgtggagac acggccagat ctgccctcca gcctgatctt ttggccagaa ggagattaaa  120
aagatgcccc tcaagatggc aagggcgaat tcgtttaaac ctgca                  165

SEQ ID NO: 45              moltype = DNA   length = 88
FEATURE                    Location/Qualifiers
misc_feature               1..88
                           note = Description of Artificial Sequence: Synthetic
                            oligonucleotide
source                     1..88
                           mol_type = other DNA
                           organism = synthetic construct
SEQUENCE: 45
cctgtgacct gtggagacac ggccagatct gccctccagc ctgatctttt ggccagaagg   60
agattaaaaa gatgcccctc aagatggc                                      88

SEQ ID NO: 46              moltype = DNA   length = 135
FEATURE                    Location/Qualifiers
misc_feature               1..135
                           note = Description of Artificial Sequence: Synthetic
                            polynucleotide
source                     1..135
                           mol_type = other DNA
                           organism = synthetic construct
SEQUENCE: 46
tagcggccgc gaattcgccc ttcctgtgac ctgtggagac acggccagat ctgccctcca   60
gcctgatctt ttggccagaa ggagattaaa aagatgcccc tcaagatggc aagggcgaat  120
tcgtttaaac ctgca                                                    135
```

-continued

```
SEQ ID NO: 47            moltype = DNA   length = 135
FEATURE                  Location/Qualifiers
misc_feature             1..135
                         note = Description of Artificial Sequence: Synthetic
                          polynucleotide
source                   1..135
                         mol_type = other DNA
                         organism = synthetic construct
SEQUENCE: 47
tagcggccgc gaattcgccc ttcctgtgac ctgtggagac acggccagat ctgccctcca   60
gcctgatctt ttggccagaa ggagattaaa aagatgcccc tcaagatggc aagggcgaat  120
tcgtttaaac ctgca                                                   135

SEQ ID NO: 48            moltype = DNA   length = 133
FEATURE                  Location/Qualifiers
misc_feature             1..133
                         note = Description of Artificial Sequence: Synthetic
                          polynucleotide
source                   1..133
                         mol_type = other DNA
                         organism = synthetic construct
SEQUENCE: 48
gcggccgcga attcgccctt cctgtgacct gtggagacac ggccagatct gccctccagc   60
ctgatctttt ggccagaagg agattaaaaa gatgccctc aagatggcaa gggcgaattc  120
gtttaaacct gca                                                     133

SEQ ID NO: 49            moltype = DNA   length = 83
FEATURE                  Location/Qualifiers
misc_feature             1..83
                         note = Description of Artificial Sequence: Synthetic
                          oligonucleotide
source                   1..83
                         mol_type = other DNA
                         organism = synthetic construct
SEQUENCE: 49
gccctccagc ctgatctttt ggccagaagg agattaaaaa gatgccctc aagatggcaa   60
gggcgaattc gtttaaacct gca                                           83

SEQ ID NO: 50            moltype = DNA   length = 68
FEATURE                  Location/Qualifiers
misc_feature             1..68
                         note = Description of Artificial Sequence: Synthetic
                          oligonucleotide
source                   1..68
                         mol_type = other DNA
                         organism = synthetic construct
SEQUENCE: 50
cttttggcca gaaggagatt aaaaagatgc ccctcaagat ggcaagggcg aattcgttta   60
aacctgca                                                            68

SEQ ID NO: 51            moltype = DNA   length = 66
FEATURE                  Location/Qualifiers
misc_feature             1..66
                         note = Description of Artificial Sequence: Synthetic
                          oligonucleotide
source                   1..66
                         mol_type = other DNA
                         organism = synthetic construct
SEQUENCE: 51
tttggccaga aggagattaa aaagatgccc ctcaagatgg caagggcgaa ttcgtttaaa   60
cctgca                                                              66

SEQ ID NO: 52            moltype = DNA   length = 66
FEATURE                  Location/Qualifiers
misc_feature             1..66
                         note = Description of Artificial Sequence: Synthetic
                          oligonucleotide
source                   1..66
                         mol_type = other DNA
                         organism = synthetic construct
SEQUENCE: 52
tttggccaga aggagattaa aaagatgccc ctcaagatgg caagggcgaa ttcgtttaaa   60
cctgca                                                              66

SEQ ID NO: 53            moltype = DNA   length = 137
FEATURE                  Location/Qualifiers
misc_feature             1..137
                         note = Description of Artificial Sequence: Synthetic
```

-continued

```
                         polynucleotide
source                   1..137
                         mol_type = other DNA
                         organism = synthetic construct
SEQUENCE: 53
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgca                                                 137

SEQ ID NO: 54           moltype = DNA   length = 137
FEATURE                 Location/Qualifiers
misc_feature            1..137
                         note = Description of Artificial Sequence: Synthetic
                         polynucleotide
source                   1..137
                         mol_type = other DNA
                         organism = synthetic construct
SEQUENCE: 54
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgca                                                 137

SEQ ID NO: 55           moltype = DNA   length = 137
FEATURE                 Location/Qualifiers
misc_feature            1..137
                         note = Description of Artificial Sequence: Synthetic
                         polynucleotide
source                   1..137
                         mol_type = other DNA
                         organism = synthetic construct
SEQUENCE: 55
tttagcggcc gcgaattcgc ccttcctgtg acctgtggag acacggccag atctgccctc   60
cagcctgatc ttttggccag aaagagatta aaaagatgcc cctcaagatg gcaagggcga  120
attcgtttaa acctgca                                                 137

SEQ ID NO: 56           moltype = DNA   length = 137
FEATURE                 Location/Qualifiers
misc_feature            1..137
                         note = Description of Artificial Sequence: Synthetic
                         polynucleotide
source                   1..137
                         mol_type = other DNA
                         organism = synthetic construct
SEQUENCE: 56
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgca                                                 137

SEQ ID NO: 57           moltype = DNA   length = 137
FEATURE                 Location/Qualifiers
misc_feature            1..137
                         note = Description of Artificial Sequence: Synthetic
                         polynucleotide
source                   1..137
                         mol_type = other DNA
                         organism = synthetic construct
SEQUENCE: 57
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgca                                                 137

SEQ ID NO: 58           moltype = DNA   length = 137
FEATURE                 Location/Qualifiers
misc_feature            1..137
                         note = Description of Artificial Sequence: Synthetic
                         polynucleotide
source                   1..137
                         mol_type = other DNA
                         organism = synthetic construct
SEQUENCE: 58
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgca                                                 137

SEQ ID NO: 59           moltype = DNA   length = 137
FEATURE                 Location/Qualifiers
misc_feature            1..137
                         note = Description of Artificial Sequence: Synthetic
                         polynucleotide
```

```
source                   1..137
                         mol_type = other DNA
                         organism = synthetic construct
SEQUENCE: 59
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgca                                                 137

SEQ ID NO: 60            moltype = DNA   length = 88
FEATURE                  Location/Qualifiers
misc_feature             1..88
                         note = Description of Artificial Sequence: Synthetic
                         oligonucleotide
source                   1..88
                         mol_type = other DNA
                         organism = synthetic construct
SEQUENCE: 60
cctgtgacct gtggagacac ggccagatct gccctccagc ctgatctttt ggccagaagg   60
agattaaaaa gatgccctc aagatggc                                       88

SEQ ID NO: 61            moltype = DNA   length = 137
FEATURE                  Location/Qualifiers
misc_feature             1..137
                         note = Description of Artificial Sequence: Synthetic
                         polynucleotide
source                   1..137
                         mol_type = other DNA
                         organism = synthetic construct
SEQUENCE: 61
tttagcggcc gcgaattcgc ccttcctgtg acctgtggag acacggccag atctgccctc   60
cagcctgatc ttttggccag aaagagatta aaaagatgcc cctcaagatg gcaagggcga  120
attcgtttaa acctgca                                                 137

SEQ ID NO: 62            moltype = DNA   length = 137
FEATURE                  Location/Qualifiers
misc_feature             1..137
                         note = Description of Artificial Sequence: Synthetic
                         polynucleotide
source                   1..137
                         mol_type = other DNA
                         organism = synthetic construct
SEQUENCE: 62
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgca                                                 137

SEQ ID NO: 63            moltype = DNA   length = 137
FEATURE                  Location/Qualifiers
misc_feature             1..137
                         note = Description of Artificial Sequence: Synthetic
                         polynucleotide
source                   1..137
                         mol_type = other DNA
                         organism = synthetic construct
SEQUENCE: 63
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgca                                                 137

SEQ ID NO: 64            moltype = DNA   length = 136
FEATURE                  Location/Qualifiers
misc_feature             1..136
                         note = Description of Artificial Sequence: Synthetic
                         polynucleotide
source                   1..136
                         mol_type = other DNA
                         organism = synthetic construct
SEQUENCE: 64
ttagcggccg cgaattcgcc cttcctgtga cctgtggaga cacggccaga tctgccctcc   60
agcctgatct tttggccaga aggagattaa aaagatgccc ctcaagatgg caagggcgaa  120
ttcgtttaaa cctgca                                                  136

SEQ ID NO: 65            moltype = DNA   length = 133
FEATURE                  Location/Qualifiers
misc_feature             1..133
                         note = Description of Artificial Sequence: Synthetic
                         polynucleotide
source                   1..133
                         mol_type = other DNA
```

```
                              organism = synthetic construct
SEQUENCE: 65
gcggccgcga attcgccctt cctgtgacct gtggagacac ggccagatct gccctccagc    60
ctgatctttt ggccagaagg agattaaaaa gatgccctc aagatggcaa gggcgaattc   120
gtttaaacct gca                                                      133

SEQ ID NO: 66              moltype = DNA   length = 133
FEATURE                    Location/Qualifiers
misc_feature               1..133
                           note = Description of Artificial Sequence: Synthetic
                            polynucleotide
source                     1..133
                           mol_type = other DNA
                           organism = synthetic construct
SEQUENCE: 66
gcggccgcga attcgccctt cctgtgacct gtggagacac ggccagatct gccctccagc    60
ctgatctttt ggccagaagg agattaaaaa gatgccctc aagatggcaa gggcgaattc   120
gtttaaacct gca                                                      133

SEQ ID NO: 67              moltype = DNA   length = 65
FEATURE                    Location/Qualifiers
misc_feature               1..65
                           note = Description of Artificial Sequence: Synthetic
                            oligonucleotide
source                     1..65
                           mol_type = other DNA
                           organism = synthetic construct
SEQUENCE: 67
ttggccagaa ggagattaaa aagatgcccc tcaagatggc aagggcgaat tcgtttaaac    60
ctgca                                                                65

SEQ ID NO: 68              moltype = DNA   length = 135
FEATURE                    Location/Qualifiers
misc_feature               1..135
                           note = Description of Artificial Sequence: Synthetic
                            polynucleotide
source                     1..135
                           mol_type = other DNA
                           organism = synthetic construct
SEQUENCE: 68
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctg                                                    135

SEQ ID NO: 69              moltype = DNA   length = 135
FEATURE                    Location/Qualifiers
misc_feature               1..135
                           note = Description of Artificial Sequence: Synthetic
                            polynucleotide
source                     1..135
                           mol_type = other DNA
                           organism = synthetic construct
SEQUENCE: 69
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctg                                                    135

SEQ ID NO: 70              moltype = DNA   length = 135
FEATURE                    Location/Qualifiers
misc_feature               1..135
                           note = Description of Artificial Sequence: Synthetic
                            polynucleotide
source                     1..135
                           mol_type = other DNA
                           organism = synthetic construct
SEQUENCE: 70
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctg                                                    135

SEQ ID NO: 71              moltype = DNA   length = 112
FEATURE                    Location/Qualifiers
misc_feature               1..112
                           note = Description of Artificial Sequence: Synthetic
                            polynucleotide
source                     1..112
                           mol_type = other DNA
                           organism = synthetic construct
SEQUENCE: 71
```

```
tttagcggcc gcgaattcgc ccttcctgtg acctgtggag acacggccag atctgccctc  60
cagcctgatc ttttggccag aaggagatta aaaagatgcc cctcaagatg gc           112

SEQ ID NO: 72          moltype = DNA   length = 48
FEATURE                Location/Qualifiers
misc_feature           1..48
                       note = Description of Artificial Sequence: Synthetic
                        oligonucleotide
source                 1..48
                       mol_type = other DNA
                       organism = synthetic construct
SEQUENCE: 72
tttagcggcc gcgaattcgc ccttcctgtg acctgtggag acacggcc               48

SEQ ID NO: 73          moltype = DNA   length = 135
FEATURE                Location/Qualifiers
misc_feature           1..135
                       note = Description of Artificial Sequence: Synthetic
                        polynucleotide
source                 1..135
                       mol_type = other DNA
                       organism = synthetic construct
SEQUENCE: 73
tttagcggcc gcgaattcgc ccttcctgtg acctgtggag acacggccag atctgccctc  60
cagcctgatc ttttggccag aaggagatta aaaagatgcc cctcaagatg gcaagggcga  120
attcgtttaa acctg                                                   135

SEQ ID NO: 74          moltype = DNA   length = 88
FEATURE                Location/Qualifiers
misc_feature           1..88
                       note = Description of Artificial Sequence: Synthetic
                        oligonucleotide
source                 1..88
                       mol_type = other DNA
                       organism = synthetic construct
SEQUENCE: 74
cctgtgacct gtggagacac ggccagatct gccctccagc ctgatctttt ggccagaagg  60
agattaaaaa gatgcccctc aagatggc                                     88

SEQ ID NO: 75          moltype = DNA   length = 135
FEATURE                Location/Qualifiers
misc_feature           1..135
                       note = Description of Artificial Sequence: Synthetic
                        polynucleotide
source                 1..135
                       mol_type = other DNA
                       organism = synthetic construct
SEQUENCE: 75
tttagcggcc gcgaattcgc ccttcctgtg acctgtggag acacggccag atctgccctc  60
cagcctgatc ttttggccag aaggagatta aaaagatgcc cctcaagatg gcaagggcga  120
attcgtttaa acctg                                                   135

SEQ ID NO: 76          moltype = DNA   length = 135
FEATURE                Location/Qualifiers
misc_feature           1..135
                       note = Description of Artificial Sequence: Synthetic
                        polynucleotide
source                 1..135
                       mol_type = other DNA
                       organism = synthetic construct
SEQUENCE: 76
tttagcggcc gcgaattcgc ccttcctgtg acctgtggag acacggccag atctgccctc  60
cagcctgatc ttttggccag aaggagatta aaaagatgcc cctcaagatg gcaagggcga  120
attcgtttaa acctg                                                   135

SEQ ID NO: 77          moltype = DNA   length = 135
FEATURE                Location/Qualifiers
misc_feature           1..135
                       note = Description of Artificial Sequence: Synthetic
                        polynucleotide
source                 1..135
                       mol_type = other DNA
                       organism = synthetic construct
SEQUENCE: 77
tttagcggcc gcgaattcgc ccttcctgtg acctgtggag acacggccag atctgccctc  60
cagcctgatc ttttggccag aaggagatta aaaagatgcc cctcaagatg gcaagggcga  120
attcgtttaa acctg                                                   135

SEQ ID NO: 78          moltype = DNA   length = 133
```

```
FEATURE              Location/Qualifiers
misc_feature         1..133
                     note = Description of Artificial Sequence: Synthetic
                     polynucleotide
source               1..133
                     mol_type = other DNA
                     organism = synthetic construct
SEQUENCE: 78
tagcggccgc gaattcgccc ttcctgtgac ctgtggagac acggccagat ctgccctcca    60
gcctgatctt ttggccagaa ggagattaaa aagatgcccc tcaagatggc aagggcgaat   120
tcgtttaaac ctg                                                       133

SEQ ID NO: 79        moltype = DNA   length = 66
FEATURE              Location/Qualifiers
misc_feature         1..66
                     note = Description of Artificial Sequence: Synthetic
                     oligonucleotide
source               1..66
                     mol_type = other DNA
                     organism = synthetic construct
SEQUENCE: 79
cttttggcca gaaggagatt aaaaagatgc ccctcaagat ggcaagggcg aattcgttta    60
aacctg                                                                66

SEQ ID NO: 80        moltype = DNA   length = 61
FEATURE              Location/Qualifiers
misc_feature         1..61
                     note = Description of Artificial Sequence: Synthetic
                     oligonucleotide
source               1..61
                     mol_type = other DNA
                     organism = synthetic construct
SEQUENCE: 80
ggccagaagg agattaaaaa gatgccctc aagatggcaa gggcgaattc gtttaaacct    60
g                                                                     61

SEQ ID NO: 81        moltype = DNA   length = 109
FEATURE              Location/Qualifiers
misc_feature         1..109
                     note = Description of Artificial Sequence: Synthetic
                     polynucleotide
source               1..109
                     mol_type = other DNA
                     organism = synthetic construct
SEQUENCE: 81
tttagcggcc gcgaattcgc ccttcctgtg acctgtggag acacggccag atctgccctc    60
cagcctgatc ttttggccag aaggagatta aaaagatgcc cctcaagat                109

SEQ ID NO: 82        moltype = DNA   length = 136
FEATURE              Location/Qualifiers
misc_feature         1..136
                     note = Description of Artificial Sequence: Synthetic
                     polynucleotide
source               1..136
                     mol_type = other DNA
                     organism = synthetic construct
SEQUENCE: 82
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                    136

SEQ ID NO: 83        moltype = DNA   length = 136
FEATURE              Location/Qualifiers
misc_feature         1..136
                     note = Description of Artificial Sequence: Synthetic
                     polynucleotide
source               1..136
                     mol_type = other DNA
                     organism = synthetic construct
SEQUENCE: 83
tttagcggcc gcgaattcgc ccttcctgtg acctgtggag acacggccag atctgccctc    60
cagcctgatc ttttggccag aaggagatta aaaagatgcc cctcaagatg gcaagggcga   120
attcgtttaa acctgc                                                    136

SEQ ID NO: 84        moltype = DNA   length = 136
FEATURE              Location/Qualifiers
misc_feature         1..136
                     note = Description of Artificial Sequence: Synthetic
                     polynucleotide
```

-continued

```
source                        1..136
                              mol_type = other DNA
                              organism = synthetic construct
SEQUENCE: 84
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgc                                                  136

SEQ ID NO: 85                 moltype = DNA   length = 136
FEATURE                       Location/Qualifiers
misc_feature                  1..136
                              note = Description of Artificial Sequence: Synthetic
                               polynucleotide
source                        1..136
                              mol_type = other DNA
                              organism = synthetic construct
SEQUENCE: 85
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgc                                                  136

SEQ ID NO: 86                 moltype = DNA   length = 109
FEATURE                       Location/Qualifiers
misc_feature                  1..109
                              note = Description of Artificial Sequence: Synthetic
                               polynucleotide
source                        1..109
                              mol_type = other DNA
                              organism = synthetic construct
SEQUENCE: 86
tttagcggcc gcgaattcgc ccttcctgtg acctgtggag acacggccag atctgccctc   60
cagcctgatc ttttggccag aaggagatta aaaagatgcc cctcaagat                109

SEQ ID NO: 87                 moltype = DNA   length = 136
FEATURE                       Location/Qualifiers
misc_feature                  1..136
                              note = Description of Artificial Sequence: Synthetic
                               polynucleotide
source                        1..136
                              mol_type = other DNA
                              organism = synthetic construct
SEQUENCE: 87
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgc                                                  136

SEQ ID NO: 88                 moltype = DNA   length = 88
FEATURE                       Location/Qualifiers
misc_feature                  1..88
                              note = Description of Artificial Sequence: Synthetic
                               oligonucleotide
source                        1..88
                              mol_type = other DNA
                              organism = synthetic construct
SEQUENCE: 88
cctgtgacct gtggagacac ggccagatct gccctccagc ctgatctttt ggccagaagg   60
agattaaaaa gatgcccctc aagatggc                                      88

SEQ ID NO: 89                 moltype = DNA   length = 136
FEATURE                       Location/Qualifiers
misc_feature                  1..136
                              note = Description of Artificial Sequence: Synthetic
                               polynucleotide
source                        1..136
                              mol_type = other DNA
                              organism = synthetic construct
SEQUENCE: 89
tttagcggcc gcgaattcgc ccttcctgtg acctgtggag acacggccag atctgccctc   60
cagcctgatc ttttggccag aaggagatta aaaagatgcc cctcaagatg gcaagggcga  120
attcgtttaa acctgc                                                  136

SEQ ID NO: 90                 moltype = DNA   length = 136
FEATURE                       Location/Qualifiers
misc_feature                  1..136
                              note = Description of Artificial Sequence: Synthetic
                               polynucleotide
source                        1..136
                              mol_type = other DNA
                              organism = synthetic construct
```

-continued

```
SEQUENCE: 90
tttagcggcc gcgaattcgc ccttcctgtg acctgtggag acacggccag atctgccctc   60
cagcctgatc ttttggccag aaggagatta aaaagatgcc cctcaagatg gcaagggcga   120
attcgtttaa acctgc                                                   136

SEQ ID NO: 91              moltype = DNA  length = 136
FEATURE                    Location/Qualifiers
misc_feature               1..136
                           note = Description of Artificial Sequence: Synthetic
                            polynucleotide
source                     1..136
                           mol_type = other DNA
                           organism = synthetic construct
SEQUENCE: 91
tttagcggcc gcgaattcgc ccttcctgtg acctgtggag acacggccag atctgccctc   60
cagcctgatc ttttggccag aaggagatta aaaagatgcc cctcaagatg gcaagggcga   120
attcgtttaa acctgc                                                   136

SEQ ID NO: 92              moltype = DNA  length = 134
FEATURE                    Location/Qualifiers
misc_feature               1..134
                           note = Description of Artificial Sequence: Synthetic
                            polynucleotide
source                     1..134
                           mol_type = other DNA
                           organism = synthetic construct
SEQUENCE: 92
tagcggccgc gaattcgccc ttcctgtgac ctgtggagac acggccagat ctgccctcca   60
gcctgatctt ttggccagaa ggagattaaa aagatgcccc tcaagatggc aagggcgaat   120
tcgtttaaac ctgc                                                     134

SEQ ID NO: 93              moltype = DNA  length = 133
FEATURE                    Location/Qualifiers
misc_feature               1..133
                           note = Description of Artificial Sequence: Synthetic
                            polynucleotide
source                     1..133
                           mol_type = other DNA
                           organism = synthetic construct
SEQUENCE: 93
agcggccgcg aattcgccct tcctgtgacc tgtggagaca cggccagatc tgccctccag   60
cctgatcttt tggccagaag gagattaaaa agatgcccct caagatggca agggcgaatt   120
cgtttaaacc tgc                                                      133

SEQ ID NO: 94              moltype = DNA  length = 84
FEATURE                    Location/Qualifiers
misc_feature               1..84
                           note = Description of Artificial Sequence: Synthetic
                            oligonucleotide
source                     1..84
                           mol_type = other DNA
                           organism = synthetic construct
SEQUENCE: 94
ctgccctcca gcctgatctt ttggccagaa ggagattaaa aagatgcccc tcaagatggc   60
aagggcgaat cgtttaaac ctgc                                           84

SEQ ID NO: 95              moltype = DNA  length = 67
FEATURE                    Location/Qualifiers
misc_feature               1..67
                           note = Description of Artificial Sequence: Synthetic
                            oligonucleotide
source                     1..67
                           mol_type = other DNA
                           organism = synthetic construct
SEQUENCE: 95
cttttggcca gaaggagatt aaaaagatgc ccctcaagat ggcaagggcg aattcgttta   60
aacctgc                                                             67
```

ROLE OF PVT1 IN THE DIAGNOSIS AND TREATMENT OF MYC-DRIVEN CANCER

CROSS-REFERENCE TO RELATED APPLICATIONS

Any and all priority claims identified in the Application Data sheet, or any correction thereto, are hereby incorporated by reference under 37 CFR 1.57. For example, this application is a divisional application of U.S. patent application Ser. No. 17/053,328, filed Nov. 5, 2020, which is a U.S. national stage application of International Patent Application No. PCT/US2019/031349, filed May 8, 2019, which claims the benefit of U.S. Provisional Application No. 62/668,638, filed May 8, 2018, all of which are incorporated herein by reference in their entirety.

STATEMENT AS TO FEDERALLY SPONSORED RESEARCH

This invention was made with government support under W81XWH-17-1-0461 awarded by the Medical Research and Development Command, and R01 CA200643 awarded by the National Institutes of Health. The government has certain rights in the invention.

SEQUENCE LISTING

The instant application contains a Sequence Listing which has been submitted in XML file format and is hereby incorporated by reference in its entirety. Said XML copy, created on Oct. 26, 2023, is named 42256-733_401_SL.XML and is 649,294 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties.

BACKGROUND OF THE DISCLOSURE

There is a need to for improved diagnosis and therapeutic targeting of MYC-driven cancers.

SUMMARY OF THE DISCLOSURE

The instant disclosure is based on the observation that PVT1 splice variants are related to c-MYC driven cancers, and further in-depth characterization of the PVT1 splice variants revealed insightful components for therapeutic and diagnostic use.

One embodiment provides a method of identifying a subject as having a MYC-driven cancer, comprising: detecting a presence of a PVT1 splice variant or a peptide encoded by the PVT1 splice variant (PEP) in a biological sample isolated from said subject, and identifying said subject as having a MYC-driven cancer based on the presence of the PVT1 splice variant or the PEP, wherein the PVT1 splice variant comprises PVT1_212. In some embodiments, the method further comprises measuring the expression level of a circular PVT1_212 RNA, PVT1_212 splice variant, or PEP, or both, in the biological sample. In some embodiments, the method further comprises measuring the expression level of c-Myc or MYC, or both, in the biological sample.

In some embodiments, the PEP is a PEPc.

In some embodiments, the PEPc comprises 104 amino acids. In some embodiments, the method comprises measuring the expression level of the PEPc in the biological sample. In some embodiments, the biological sample is a liquid sample. In some embodiments, the liquid sample comprises blood or plasma. In some embodiments, the PEPc comprises a liquid biopsy biomarker for identifying if said subject has a MYC-driven cancer.

In some embodiments, the PEP comprises $PEP_L$. In some embodiments, $PEP_L$ comprises 149 amino acids. In some embodiments, the presence or expression levels of the PEP are measured using an antibody against PEPc, an antibody against $PEP_L$, or both.

In some embodiments, the method comprises identifying said subject as having a MYC-driven 8q24 gain cancer. This is determined, in some cases, by the presence of the PVT1_212 splice variant or increased expression level of the PVT_212 splice variant, or the PEP (PEPc or $PEP_L$) relative to reference values. In some embodiments, the method comprises identifying said subject as having a MYC-driven 8q24 gain medulloblastoma, based on an expression level of the PVT1_212 splice variant in the biological sample, wherein the biological sample is a tumor sample isolated from said subject.

In some embodiments, the method further comprises stratifying said subject as a subgroup 3, subgroup 4, Wnt, or Shh type medulloblastoma, based on the expression level of the PVT1_212 splice variant in the tumor sample.

In some embodiments, said subject is stratified as having a subgroup 3 type medulloblastoma if PVT1_212 splice variant expression level is 200 to 1000 fold elevated compared to a reference value. In some embodiments, said subject is stratified as having a subgroup 3, Wnt, or Shh type medulloblastoma if PVT1_212 splice variant expression level is 15 to 200 fold elevated compared to a reference value.

In some embodiments, said subject is stratified as having a subgroup 4 type medulloblastoma if PVT1_212 splice variant expression level is 0 to 15 fold elevated compared to a reference value.

In some embodiments, said subject is identified as having a MYC-driven 8q24 gain medulloblastoma if PVT1_212 splice variant expression level is 200 to 1000 fold elevated compared to a reference value. In some embodiments, the method comprises identifying said subject as having a MYC-driven 8q24 gain cancer, based on an expression level of the PVT1_212 splice variant in the biological sample, wherein the biological sample comprises a tumor sample isolated from said subject. In some embodiments, said subject is identified as having a MYC-driven 8q24 gain cancer if the expression level of the PVT1_212 splice variant is 200 to 1000 fold elevated compared to a reference value. In some embodiments, the reference value comprises expression level of the PVT1_212 splice variant in a biological sample isolated from a subject who does not have a cancer. In some embodiments, the biological sample comprises a tumor sample isolated from said subject and wherein the reference value comprises expression level of the PVT1_212 splice variant in a non-tumor sample from said subject.

One embodiment provides a method of treating cancer in a subject, comprising administering an agent that inhibits a PVT1 splice variant or a peptide encoded by the PVT1 splice variant (PEP), wherein said subject has been identified as having a MYC-driven cancer according to the method of any one of above embodiments.

One embodiment provides a method for selecting a therapy for treating a subject who has a cancer characterized by gain of c-myc, the method comprising (i) detecting a presence of a PVT1 splice variant or a peptide encoded by the PVT1 splice variant (PEP) in a biological sample isolated from said subject, wherein the PVT1 splice variant comprises PVT1_212; and (ii) selecting a therapy comprising an agent that inhibits the PEP for treating said cancer in said subject, if the PVT1 splice variant or the PEP is detected in step (i). In some embodiments, said subject has previously identified as having a cancer characterized by a co-gain of PVT1 and c-Myc. In some embodiments, the co-gain is identified by assaying the copy numbers of PVT1 and c-Myc in the same or a distinct biological sample isolated from said subject and comparing the copy numbers to reference values. In some embodiments, the reference values are copy numbers of PVT1 and c-Myc in a biological sample isolated from a subject who does not have a cancer. In some embodiments, the same or distinct biological sample comprises a tumor sample isolated from said subject and wherein the reference values are copy numbers of PVT1 and c-Myc in a non-tumor sample isolated from said subject. In some embodiments, the co-gain is identified by assaying the copy numbers of PVT1 and c-Myc in the same or a distinct biological sample and comparing with copy numbers of said genes available from the TCGA or ENSEMBL database. In some embodiments, step (i) comprises detecting the presence of the PEP using an anti-PEP antibody, a chromosomal probe specific for the 8q24 locus, or a combination of both. In some embodiments, step (i) comprises measuring the expression level of c-Myc in the biological sample before and after the biological sample is treated with an agent that is specific for exon 3 of the PVT1_212 splice variant, and wherein a reduced expression of c-Myc after treatment of the sample with the agent is indicative of the presence of the PVT1_212 splice variant. In some embodiments, the cancer comprises a 8q24.21 gain cancer. In some embodiments, the cancer comprises medulloblastoma, breast cancer, ovarian cancer, lung cancer, prostate cancer, or a colorectal cancer. In some embodiments, the same or distinct biological sample comprises a biological fluid sample. In some embodiments, the same or distinct biological sample comprises a tumor sample. In some embodiments, the tumor sample comprises a tissue biopsy or a resection.

One embodiment provides a method for characterizing a cancer in a subject, the method comprising: determining a gene expression level of a PVT1 splice variant PVT1_212 in a biological sample isolated from said subject, and characterizing the cancer as a MYC-driven cancer if expression levels of the PVT1_212 is higher than a reference value.

One embodiment provides a method for characterizing a cancer in a subject, the method comprising: detecting a presence of a PVT1 splice variant PVT1_212 in a biological sample isolated from said subject, and characterizing the cancer as a MYC-driven cancer if the PVT1 splice variant is detected in the biological sample.

One embodiment provides a method of treating a cancer in a subject, the method comprising: detecting a presence of a PVT1 splice variant PVT1_212 in a biological sample isolated from said subject, and administering a therapy targeting a peptide encoded by the PVT1_212, wherein said peptide comprises PEPc or PEP$_L$. In some embodiments, said subject has previously identified as having a cancer characterized by a co-gain of PVT1 and c-Myc. In some embodiments, the co-gain is identified by assaying copy numbers of PVT1 and c-Myc in the same or a distinct biological sample isolated from said subject and comparing the copy numbers to reference values. In some embodiments, the reference values are the copy numbers of PVT1 and c-Myc in a biological sample isolated from a subject who does not have a cancer. In some embodiments, the reference values are the copy numbers of PVT1 and c-Myc in a non-tumor sample isolated from said subject. In some embodiments, the co-gain is identified by assaying the copy numbers of PVT1 and c-Myc in the same or a distinct tumor sample isolated from said subject and comparing with copy numbers of said genes available from the TCGA or ENSEMBL database. In some embodiments, the cancer comprises a 8q24.21 gain cancer. In some embodiments, the cancer comprises medulloblastoma, breast cancer, ovarian cancer, lung cancer, prostate cancer, or a colorectal cancer.

One embodiment provides a method of treating a cancer in a subject, the method comprising administering a therapy targeting a peptide encoded by a PVT1 splice variant PVT1_212, wherein the subject has previously been identified as having a cancer characterized by co-gain of PVT1 and c-Myc, wherein said peptide comprises PEPc or PEP$_L$. In some embodiments, the co-gain is identified by assaying copy numbers of PVT1 and c-Myc in a biological sample isolated from said subject and comparing the copy numbers to reference values. In some embodiments, the reference values are the copy numbers of PVT1 and c-Myc in a biological sample isolated from a subject who does not have a cancer. In some embodiments, the reference values are the copy numbers of PVT1 and c-Myc in a non-tumor sample isolated from said subject. In some embodiments, the co-gain is identified by assaying copy numbers of PVT1 and c-Myc in a tumor sample isolated from said subject and comparing with copy numbers of said genes available from the TCGA or ENSEMBL database. In some embodiments, the cancer comprises a 8q24.21 gain cancer. In some embodiments, the cancer comprises medulloblastoma, breast cancer, ovarian cancer, lung cancer, prostate cancer, or a colorectal cancer.

DETAILED DESCRIPTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The term "gene," as used herein, refers to a segment of nucleic acid that encodes an individual protein or RNA (also referred to as a "coding sequence" or "coding region"), optionally together with associated regulatory regions such as promoters, operators, terminators and the like, which may be located upstream or downstream of the coding sequence.

The terms "treat," "treating," and "treatment" is meant to include alleviating or abrogating a disorder, disease, or condition; or one or more of the symptoms associated with the disorder, disease, or condition; or alleviating or eradicating the cause(s) of the disorder, disease, or condition itself. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The term "therapeutically effective amount" refers to the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "MYC-driven cancer," refers to a cancer characterized by aberrant (typically augmented expression) expression of the c-Myc gene or the MYC protein.

Methods of Diagnosis and Treatment

PVT1, a 'long non-coding RNA' adjacent to prominent oncogene c-Myc, has been shown to co-operate with c-Myc by stabilizing its protein product (MYC) in 8q24 gain cancers (Tseng et al. Nature 512, 82-86, 2014, the correlation is illustrated in FIG. 1 of U.S. Publication No. 2021/0071266 A1, which is incorporated by reference herein in its entirety). The present disclosure identifies that targeting PVT1 in 8q24 gain cancers provides a therapeutic window to target MYC, an otherwise notoriously undruggable candidate in cancers. Provided herein in one embodiment are methods of identifying a subject as having a MYC-driven cancer by identifying a PVT1 splice variant in a biological sample isolated from the subject. The PVT1 splice variant comprises PVT1_212, in certain embodiments. The method further comprises identifying a cancer subtype in a subject by detecting a presence or expression level of the PVT1_212 splice variant in a biological sample, such as a liquid sample, a tumor sample, or a non-tumor sample. In some embodiments, c-Myc gene expression level is measured in the biological sample along with detection/measurement of PVT1_212 presence or expression levels. In another embodiment, the copy number of PVT1_212, either alone or in combination with the copy number of c-Myc gene, is identified to diagnose a 8q24 gain MYC-driven cancer. Various methods can be used to identify the PVT1_212 splice variant, such as antibody-based detection, quantitative PCR. Upon detection of the PVT1_212 in the biological sample and assaying its expression level, it is possible to identify the cancer as a MYC-driven cancer. In some embodiments, the cancer is medulloblastoma, and the method disclosed herein enables stratification of the medulloblastoma as Subgroup 3, Subgroup 4, Wnt, or Shh type medulloblastoma based on the expression level of the PVT1_212 splice variant, particularly, the elevated expression level compared to reference values. The reference values are, for instance, in biological samples isolated from a subject who does not have cancer, or a non-tumor sample from the same subject whose tumor sample has elevated PVT1_212. In some embodiments, the expression level of PVT1_212 splice variant is elevated greater than about 2-fold, or about 3-fold, or about 4-fold, or about 5-fold, or about 6-fold, or about 7-fold, or about 8-fold, or about 9-fold, or about 10-fold, or about 11-fold, or about 12-fold, or about 13-fold, or about 14-fold, or about 15-fold, or about 16-fold, or about 17-fold, or about 18-fold, or about 19-fold, or about 20 fold or more compared to a reference value.

It is also identified herein that PVT1_212 undergoes backsplicing and form a circular RNA (CircPVT1_212). Since circular RNAs are more stable than linear RNAs due to their resistance to exonucleases, and can be identified in blood/plasma derived patient samples, this disclosure identifies that, in some cases, the CircPVT1_212 is used as a liquid biopsy marker for MYC-driven, 8q24 gain cancers.

This disclosure further identifies a PVT1_212 splice variant peptide encoded upon circularization (PEPc) and a peptide encoded by the linear form (PEP$_L$). In a further embodiment, several antibodies against the C terminal of PEPc and PEP$_L$ which can identify endogenous expression of the PEPs are provided. In some embodiment, these antibodies are used against the PVT variations for histopathology, research, and diagnostic purpose for 8q24 gained, MYC-driven cancers. Further provided are inhibitors against the PEPs (PEPc and PEP$_L$).

Provided herein is a method of detecting a novel PVT-1 splice variant in a biological sample. The method of detection involves: obtaining a biological sample from a subject, isolating a nucleic acid from the biological sample that comprises genomic DNA, and analysis for the presence or absence of the PVT-1 splice variant. In some embodiments, the method comprises detection of a protein product or a peptide encoded by the splice variant that distinguishes the splice variant from the wild type form. In some embodiments such detection involves using an antibody for western hybridization or in situ hybridization detection methods. In some embodiments, the novel PVT-1 splice variant is a circular PVT-1 transcript product. In some embodiments, the novel PVT-1 splice variant is a circular PVT-1 translated product. Identification of the novel PVT-1 splice variant indicates presence of a cMYC driven cancer in the subject.

In some embodiments, identification of any one of the PVT1 splice variants indicated in the above section of the disclosure described herein in a biological sample from a subject is indicative of a MYC-driven cancer in the subject. In some embodiments, identification of Circ PVT1 in a sample from the subject is indicative of a MYC-driven cancer in the subject. In some embodiments one or more PVT1 splice variants can be identified. In some embodiments one or more PVT1 splice variants can be the 104 amino acid PEPc in a biological sample of a subject is indicative of a MYC driven cancer in the subject.

In some embodiments identification of any one or more of the PVT1 splice variant identified in the disclosure is complemented with an additional mode of analysis of a biological sample from the subject for determination of c-MYC driven cancer in a subject.

In some embodiments identification of any one or more of the PVT1 splice variant identified in the disclosure is complemented with one or more physiological evaluations of the subject for determination of c-MYC driven cancer in a subject.

In some embodiments identification of any one or more of the PVT1 splice variant identified in the disclosure is complemented with one or more biochemical evaluations of the subject for determination of c-MYC driven cancer in a subject.

In some embodiments, identification of any one or more of the PVT1 splice variant is performed by analysis of RNA. In some embodiments, qRT-PCR analysis is used for the identification. In some embodiments the identification of any one or more of the PVT1 splice variant is performed by analysis using a PVT1-splice variant specific antibody for determination of c-MYC driven cancer in a subject.

In some embodiments provided herein is a method for treating a subject having a MYC-driven cancer, the method comprising: (a) determining the presence of one or more PVT1 splice variant in a biological sample from the subject, wherein the PVT1-splice variant augments c-MYC expression; (b) administering to the subject a therapeutic composition for the MYC-driven cancer.

Also provided herein is a kit for determining a PVT1 splice variant in a biological sample of a subject.

EXAMPLES

The examples below further illustrate the described embodiments without limiting the scope of the disclosure.

Example 1: Identification of the PVT1 Splice Variant Responsible for Stabilizing MYC Protein in Human Cancers The ENSEMBLE database was searched in order to identify the variants that regulate MYC protein in cancer cells. Accordingly, 25 splice variants of PVT1 have been found (FIG. 2 of U.S. Publication No. 2021/0071266 A1, which is incorporated by reference herein in its entirety). Primers were developed to identify the abundance of each transcript in patient derived medulloblastoma (MB) xenografts (PDX) (FIGS. 3 and 4 of U.S. Publication No. 2021/0071266 A1, which are incorporated by reference herein in their entireties). The analysis suggested that PVT1_212 is the most abundant PVT1 splice variant in all the 4 subgroups of the MB PDXs, while PVT1_203 being the second most prevalent splice variant. PVT1_212 is most prevalent in the MB Subgroup 3 patients, which has the poorest prognosis among the MB patients (FIG. 5 of U.S. Publication No. 2021/0071266 A1, which is incorporated by reference herein in its entirety). Three types of PVT1_212 expression pattern were identified in MB PDXs as well in patient samples: Low PVT1_212 expressing group (0-15×): contained mainly Subgroup 4 MBs, Intermediate PVT1_212 expressing group (15-200×): contained Subgroups 3, Shh and Wnt MB, and the high PVT1_212 expressing group (200-1000×): Exclusively Subgroup 3 (FIGS. 6 and 7 of U.S. Publication No. 2021/0071266 A1, which are incorporated by reference herein in their entireties). This demonstrated that PVT1 expression can be used to stratify MB patients, where the high PVT1_212 expressing group (200-1000×) can designate the 8q24 gain, MYC-driven type of the Group 3 MB patients (generally associated with the poor prognosis).

Example 2: Functional Identification of the PVT1 Exons Regulating MYC Protein in Human Cancers For this study, si-RNAs against exon 2, 3 and 9 of the annotated PVT1 gene were designed. Among these, exon 9 exclusively belongs to PVT1_203, whereas exon 2 and 3 is shared between PVT1_212 and PVT1_203. Knock down of PVT1 using si-RNAs against exons 2 and 3, but not Exon 9, reduced MYC protein by as much as 75% (MSTO) to 40% (NCI-H1792) (FIGS. 8, 9, 10, and 11 of U.S. Publication No. 2021/0071266 A1, which are incorporated by reference herein in their entireties). This demonstrated that PVT1_212, and not PVT1_203 was responsible for MYC augmentation in 8q24 gain cancers, and targeting the product of PVT1_212 can significantly reduce the MYC protein levels in these cancers.

Example 3: PVT1_212 Codes for Novel Peptides that Augment MYC in 8q24 Gain Cancers This study demonstrated exon 2 of the PVT1 gene can undergo back-splicing and form a circular RNA (CircPVT1_212) (FIGS. 12A-C and 13 of U.S. Publication No. 2021/0071266 A1, which are incorporated by reference herein in their entireties). As shown in FIG. 12A and FIG. 12B(i) of U.S. Publication No. 2021/0071266 A1 PVT1_212 consists of three exons and span over Ch8:127794533-Ch8:127940454. FIG. 12B(ii). cDNA was derived from total RNA obtained from cancer cells using random hexamers (it is important to use random hexamers, since circular RNAs do not have poladenylated 3' sequence). Divergent primers were designed for each exons of PVT1_212 to identify the CircPVT1 arising from exon 2 of PVT1_212. Sequencing of the CircPVT1 junction confirmed that the junction sequence emanated from the 3' and 5' ends of PVT1_212 (FIG. 12B(iii) and FIG. 12C of U.S. Publication No. 2021/0071266 A1). FIG. 12B of U.S. Publication No. 2021/0071266 A1 is a graphical representation indicating that PVT1_212 consists of three exons and span over Ch8:127794533-Ch8:127940454 (FIG. 12B[i] of U.S. Publication No. 2021/0071266 A1). Divergent primers are designed for each exon (FIG. 12B[ii] of U.S. Publication No. 2021/0071266 A1). cDNA was derived from total RNA using random hexamers and sequenced (FIG. 12B[iii] of U.S. Publication No. 2021/0071266 A1). FIG. 12C of U.S. Publication No. 2021/0071266 A1 indicates junction sequence of the CircPVT1 emanating from the 3' and 5' ends of PVT1_212 (SEQ ID NO.: 22) (highlighted). Cloning the splice junction demonstrated that this circle emanates from PVT1_212 and not PVT1_203, since the latter starts from ~150 bp downstream of the beginning of the Exon 2 (FIG. 13 of U.S. Publication No. 2021/0071266 A1, which is incorporated by reference herein in its entirety). FIG. 13 of U.S. Publication No. 2021/0071266 A1 shows the circular PVT1 RNA (SEQ ID NO: 1) in various cell lines. It was found that upon circularization, CircPVT1_212 can form a protein coding ORF of 104 amino acids. The potential peptide was designed as PVT1 Encoded Peptide upon Circularization (PEPc). It was also found that PVT1_212 can encode another peptide (from Exon 1 and 2) of 149 amino acids, which share the same ORF with PEPc for the 94 amino acids at their C terminal end. This variant was designed as PVT1 Encoded Peptide linear form (PEP$_L$) (FIG. 14 of U.S. Publication No. 2021/0071266 A1, which is incorporated by reference herein in its entirety). FIG. 14 of U.S. Publication No. 2021/0071266 A1 is a graphical representation that shows the structure of PEP. PEPc (SEQ ID NO: 33) and PEP$_L$ (SEQ ID NO: 34) are shown in FIG. 14 of U.S. Publication No. 2021/0071266 A1. Exogenous addition of PEPc and/or PEP$_L$ was seen to augment MYC in U2OS and LNCaP cells, and increase their transformation and metastatic potential (FIGS. 15 and 16 of U.S. Publication No. 2021/0071266 A1, which are incorporated by reference herein in their entireties).

The expression pattern of CircPVT1_212 was investigated in MB PDXs as well as patient samples, and it was observed that the expression of CircPVT1_212 correlates identically with PVT1_212 expression (FIGS. 17, 18, and 19 of U.S. Publication No. 2021/0071266 A1, which are incorporated by reference herein in their entireties). Since circular RNAs are typically more stable than linear RNAs due to their resistance to exonucleases, and can be identified in blood/plasma derived patient samples, this demonstrated that CircPVT1_212 can be used as a liquid biopsy marker for MYC-driven, 8q24 gain cancers. Finally, several antibodies against the C terminal of PEPc and PEP$_L$ were derived which can identify endogenous expression of the PEPs (FIGS. 20 and 21 of U.S. Publication No. 2021/0071266 A1, which are incorporated by reference herein in their entireties). Specificity of these antibodies was confirmed by knocking down PVT1_212 (FIG. 21 of U.S. Publication No. 2021/0071266 A1). This demonstrated that the antibodies against PEPs can be used for histopathology, research and diagnostic purpose for 8q24 gained, MYC-driven cancer. FIG. 22 of U.S. Publication No. 2021/0071266 A1 shows gain of 8q24 is a common amplified region in human cancer. In an exemplary assay, siRNAs that can bind to Exons 2, 3, 9, 20 and 30 of PVT1 were separately expressed in cancer cell lines MSTO and NCIH1792. It was observed that only siRNA directed to the Exon 2 and Exon 2 showed remarkable reduction in MYC protein levels (FIG. 23 of U.S. Publication No. 2021/0071266 A1, which is incorporated by reference herein in its entirety). FIG. 24 of U.S. Publication No. 2021/0071266 A1, which is incorporated by reference herein in its entirety, shows effect of siRNAs against PVT1 exons on mRNA expression of Myc in MSTO and NCIH1792 cells. FIG. 25 of U.S. Publication No. 2021/0071266 A1, which is incorporated by reference herein in its entirety, shows splice junction between exons 1 and 2 of PVT1. A portion of PVT1_212 is shown below (SEQ ID NO: 36) in FIG. 25 of U.S. Publication No. 2021/0071266 A1. The amplicon (88 bp; SEQ ID NO: 45) is spanning PVT1 exon 1-2 junction, which contains Ex12-F1 (SEQ ID NO: 35) in exon 1 and Ex12-R1 (SEQ ID NO; 37) in exon 2 as shown in FIG. 25 of U.S. Publication No. 2021/0071266 A1. Expression of Exons 1 and 2 were determined by RT-qPCR on Medulloblastoma (MedullB) samples, as shown in FIG. 26 of U.S. Publication No. 2021/0071266 A1, which is incorporated by reference herein in its entirety. The splice variants are PCR amplified with suitable primers and cloned in Topo vectors for sequence analysis as shown in FIGS. 27-29 of U.S. Publication No. 2021/0071266 A1, which are incorporated by reference herein in their entireties. FIG. 28 of U.S. Publication No. 2021/0071266 A1 shows sequence analysis of highest expression variants (For Clone M4, SEQ ID NOS 38-52, from line 1 to line 15, respectively; for Clone M5, SEQ ID NOs: 53 to 67, from line 1 to line 15, respectively). FIG. 29 of U.S. Publication No. 2021/0071266 A1 shows sequence analysis of highest expression variant (For Clone 23, SEQ ID NOS 68-80, from line 1 to line 13, respectively; for Clone 1377, SEQ ID NOs: 81 to 95, from line 1 to line 15, respectively).

Example 4: Circ PVT1 in MYC Cancers

Expression of the CircPVT1 was further investigated in patient tissue samples. CircPVT1 is enriched in MYC driven Group 3 medulloblastoma tumors. FIG. 30A of U.S. Publication No. 2021/0071266 A1, which is incorporated by reference herein in its entirety, subgroup of Group 3 medulloblastoma harbor MYC amplification and have the worst clinical outcome compared to the other medulloblastoma groups (Cavalli et al, Cancer Cell, 31:737-754). FIG. 30B of U.S. Publication No. 2021/0071266 A1, which is incorporated by reference herein in its entirety, shows results from quantitative RT-PCR analysis of patient derived xenografts (PDX samples) from medulloblastoma patients (obtained from Dr. Weschler-Reya's lab at SBP). The results revealed that the CircPVT1 is especially enriched in the MYC driven Group 3 medulloblastoma tumors.

High abundance of CircPVT1 is correlated to high MYC protein in multiple cancer cell lines. In order to examine whether abundance of CircPVT1 and MYC are correlated in multiple cancer cell lines, 4 cell lines were selected with high copy number of MYC and PVT1 (Hi-MYC cell lines: PSN-1, NCIH-2170, NCIH-1792, MSTO-211H) and 4 cell lines with MYC+PVT1 copy number neutral cell lines (Lo-MYC cell lines: U2OS, BxPC-3, DU145 and PC-3) from ATCC. These 8 cell lines represent a broad array of different types of cancers, as outlined in FIG. 31A of U.S. Publication No. 2021/0071266 A1, which is incorporated by reference herein in its entirety. It was confirmed that the Hi-MYC cell lines are enriched in MYC protein, compared to the MYC protein in Lo-MYC cell lines (FIG. 31B of U.S. Publication No. 2021/0071266 A1, which is incorporated by reference herein in its entirety). FIG. 31C of U.S. Publication No. 2021/0071266 A1, which is incorporated by reference herein in its entirety, shows results from q-RT-PCR which revealed that CircPVT1 is expressed in much higher levels in Hi-MYC cell lines compared to those in Lo-MYC cell lines.

Inhibition of CircPVT1 leads to growth arrest of Hi- and Lo-MYC cell lines. si-RNA was designed (si_C2) against the junction of the CircPVT1 which inhibits the expression of CircPVT1, but not that of PVT1_212 (FIG. 32A of U.S. Publication No. 2021/0071266 A1, which is incorporated by reference herein in its entirety). Cell proliferation was assessed by counting cells following the transfection of the Hi-MYC and Lo-MYC cell lines with si_C2 (in red, also indicated by an arrow) and control si (si_Ctr, in blue) over the indicated period in the X-axis in in FIG. 32B of U.S. Publication No. 2021/0071266 A1, which is incorporated by reference herein in its entirety. In each case, the siRNA directed to CircPVT1(si_C2) inhibited proliferation of the MYC cell lines. The data demonstrates that the expression of the CircPVT1 is necessary for the proliferation of Hi-MYC as well as Lo-MYC cell lines, thus establishing the centrality of the CircPVT1 for the proliferation of cancer cells.

Next, it was investigated whether CircPVT1 can regulate MYC levels. Indeed, siRNA mediated knockdown of CircPVT1 in Hi- and Lo-MYC cell lines resulted in reduction in the MYC level in Hi-MYC as well as Lo-MYC cells, suggesting that CircPVT1 is required for MYC protein levels in cancer cells (FIG. 33 of U.S. Publication No. 2021/0071266 A1, which is incorporated by reference herein in its entirety).

It was found that circularization of RNA from Exon 2 of PVT1_212 reorganizes its reading frame, resulting into a novel open reading frame coding for 104 amino acids containing peptide, henceforth known as PEPc (PVT1 Encoded Peptide upon Circularization) or Conjoined (CJN). FIG. 34A of U.S. Publication No. 2021/0071266 A1, which is incorporated by reference herein in its entirety shows a schematic diagram of the circularized of RNA with the open reading frame indicated, with the start codon (ATG) and the stop codon (TGA), encoding PEPc. A monoclonal antibody was developed against PEPc/CJN which can detect endogenously expressed PEPc/CJN in the four Hi-MYC cell lines (FIG. 34B of U.S. Publication No. 2021/0071266 A1, which is incorporated by reference herein in its entirety). The specificity of the antibody was confirmed by carrying out a Western Blot analysis where inhibition of the CircPVT1 (by si_C2) but not of PVT1_212 (by si_3) resulted into reduction of the protein detected by the PEPc antibody (FIG. 34C of U.S. Publication No. 2021/0071266 A1, which is incorporated by reference herein in its entirety).

Expression of PEPc is sufficient to augment MYC in cancer cells. Western blot analysis of MYC protein in U2OS cells stably transfected with Luciferase (as control) or PEPc, showed increase in MYC levels on ectopic expression of PEPc (FIG. 35A of U.S. Publication No. 2021/0071266 A1, which is incorporated by reference herein in its entirety). PEPc expression increased colony formation and migration ability of U2OS (FIG. 35B of U.S. Publication No. 2021/0071266 A1, which is incorporated by reference herein in its entirety). Soft agar assay showed an increase in colony numbers compared to the control when equal number of U2OS+Luciferase and U2OS+PEPc cells are plated on soft agar. Transwell migration assay showed increase in migration potential in U2OS+PEPc cells.

Additional sequences that may be used in the methods disclosed herein include those listed in Table 1, below.

| SEQ ID NO. | Sequence | Description |
|---|---|---|
| 1 | GCCTGATCTTTTGGCCAGAAGGAGATTAAAAAGATGCCC CTCAAGATGGCTGTGCCTGTCAGCTGCATGGAGCTTCGT TCAAGTATTTTCTGAGCCTGATGGATTTACAGTGATCTT CAGTGGTCTGGGGAATAACGCTGGTGGAACCATGCACTG GAATGACACACGCCCGGCACATTTCAGGATACTAAAAGT GGTTTTAAGGGAGGCTGTGGCTGAATGCCTCATGGATTC TTACAGCTTGGATGTCCATGGGGGACGAAGGACTGCAGC TGGCTGAGAGGGTTGAGATCTCTGTTTACTTAGATCTCT GCCAACTTCCTTTGGGTCTCCCTATGGAATGTAAGACCC CGACTCTTCCTGGTGAAGCATCTGATGCACGTTCCATCC GGCGCTCAGCTGGGCTTGAG | Circular RNA of exon 2 of PVT1 splice variant PVT1_212 ("CircPVT1") |
| 2 | CCATCCGGCGCTCAG | Si_CircPVT1 or si_C2: Target sequence |
| 3 | UGGGCUUGAGGCCUGAUCUUU | Sense sequence for Si_CircPVT1 or si_C2: Target sequence |
| 4 | AGAUCAGGCCUCAAGCCCAUU | Antisense sequence for Si_CircPVT1 or si_C2: Target sequence |
| 5 | GCCATCATGATGGTACTTT | siRNA PVT1 Exon 3 target sequence |
| 6 | CAUCAUGAUGGUACU U UAATT | siRNA PVT1 Exon 3 sense strand |
| 7 | UUAAAGUACCAUCAUGAUGGC | siRNA PVT1 Exon 3 antisense strand |
| 8 | CCGGCACATTTCAGGATACTA | siRNA PVT1 Exon 2 target sequence |
| 9 | GGCACAUUUCAGGAUACUAUU | siRNA PVT1 Exon 2 target sequence |

-continued

| SEQ ID NO. | Sequence | Description |
|---|---|---|
| 10 | UAGUAUCCUGAMUGUGCCGG | siRNA PVT1 Exon 2 target sequence |
| 11 | atgcacgttccatcc ggcgctcagctgggcttgaggcctgatcttttggccagaaggaga ttaaaaagatgcccctcaagatggctgtgcctgtcagctgcatgg agcttcgttcaagtattttctgagcctgatggatttacagtgatc ttcagtggtctggggaataacgctggtggaaccatgcactggaat gacacacgcccggcacatttcaggatactaaaagtggttttaagg gaggctgtggctgaatgcctcatggattcttacagcttggatgtc catgggggacgaaggactgcagctggctga | CircPVT1's endogenously expressed 104 aa peptide ("PEPc" or "Conjoined") |
| 12 | M H V P S G A Q L G L R P D L L A R R R L K R C P S R W L C L S A A W S F V Q V F S E P D G F T V I F S G L G N N A G G T M H W N D T R P A H F R I L K V V L R E A V A E C L M D S Y S L D V H G G R R T A A G * | CircPVT1's endogenously expressed 104 aa peptide ("PEPc" or "Conjoined") |
| 13 | ATG CAC GTT CCA TCC GGC GCT CAG CTG GGC TTG AGG CCT GAT CTT TTG GCC AGA AGG AGA TTA AAA AGA TGC CCC TCA AGA TGG CTG TGC CTG TCA GCT GCA TGG AGC TTC GTT CAA GTA TTT TCT GAG CCT GAT GGA TTT ACA GTG ATC TTC AGT GGT CTG GGG AAT AAC GCT GGT GGA ACC ATG CAC TGG AAT GAC ACA CGC CCG GCA CAT TTC AGG ATA CTA AAA GTG GTT TTA AGG GAG GCT GTG GCT GAA TGC CTC ATG GAT TCT TAC AGC TTG GAT GTC CAT GGG GGA CGA AGG ACT GCA GCT GGC TGA | Original PEPc DNA |
| 14 | MHVPSGAQLGLRPDLLARRRLKRCPSRWLCLSAAWSFVQV FSEPDGFTVIFSGLGNNAGGTMHWNDTRPAHFRILKVVLR EAVAECLMDSYSLDVHGGRRTAAG | Original PEPc aa (104 aa) |
| 15 | ATG CAT GTA CCT TCC GGC GCC CAA CTC GGC CTC AGA CCG GAC CTG TTG GCC CGA CGA CGA CTG AAG CGA TGC CCT AGC AGG TGG CTC TGT CTG TCA GCT GCG TGG TCT TTT GTC CAA GTT TTC TCC GAG CCA GAT GGT TTC ACA GTT ATT TTC TCC GGG TTG GGT AAC AAT GCG GGC ACT ATG CAT TGG AAT GAT ACT AGA CCA GCA CAC TTT AGG ATC TTG AAA GTG GTC CTC AGG GAA GCG GTG GCG GAA TGT CTG ATG GAT AGT TAT TCA CTG GAC GTA CAT GGG GGT CGC CGA ACA GCC GCA GGC TGA | Codon optimized PEPc DNA |
| 16 | TGA CAC GTT CCA TCC GGC GCT CAG CTG GGC TTG AGG CCT GAT CTT TTG GCC AGA AGG AGA TTA AAA AGA TGC CCC TCA AGA TGG CTG TGC CTG TCA GCT GCA TGG AGC TTC GTT CAA GTA TTT TCT GAG CCT GAT GGA TTT ACA GTG ATC TTC AGT GGT CTG GGG AAT AAC GCT GGT GGA ACC TGA CAC TGG AAT GAC ACA CGC CCG GCA CAT TTC AGG ATA CTA AAA GTG GTT TTA AGG GAG GCT GTG GCT GAA TGC CTC TGA GAT TCT TAC AGC TTG GAT GTC CAT GGG GGA CGA AGG ACT GCA GCT GGC TGA | PEPc (ATG > TGA) DNA |

While preferred embodiments of the present disclosure have been shown and described herein, it will be obvious to those skilled in the art that such embodiments are provided by way of example only. It is not intended that the disclosed methods be limited by the specific examples provided within the specification. While the disclosed methods have been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all aspects of the disclosure are not limited to the specific depictions, configurations or relative proportions set forth herein which depend upon a variety of conditions and variables. It should be understood that various alternatives to the embodiments of the disclosed methods described herein may be employed in practicing the methods. It is therefore contemplated that the disclosure shall also cover any such alternatives, modifications, variations or equivalents. It is intended that the following claims define the scope of the disclosure and that methods and structures within the scope of these claims and their equivalents be covered thereby.

What is claimed is:

1. A method of treating a cancer in a subject, the method comprising administering to the subject a therapy targeting a PVT1 splice variant CircPVT1, wherein the therapy comprises an siRNA directed to the PVT1 splice variant CircPVT1, wherein the siRNA comprises a nucleotide sequence that is complementary to SEQ ID NO. 1 or a portion thereof, wherein the siRNA comprises the nucleotide sequence set forth in SEQ ID NO. 3 or SEQ ID NO. 4, and wherein the subject has previously been identified as having a cancer characterized by a co-gain of a PVT1 and a c-Myc.

2. The method of claim 1, wherein the co-gain is identified by assaying copy numbers of the PVT1 and the c-Myc in a biological sample isolated from the subject and comparing with copy numbers of the PVT1 and the c-Myc in a corresponding biological sample isolated from a subject who does not have the cancer.

3. The method of claim 1, wherein the co-gain is identified by assaying copy numbers of the PVT1 and the c-Myc in a biological sample isolated from the subject and comparing with copy numbers of the PVT1 and the c-Myc in a non-tumor sample isolated from the subject.

4. The method of claim 1, wherein the co-gain is identified by assaying copy numbers of the PVT1 and the c-Myc in a tumor sample isolated from the subject and comparing with copy numbers of the PVT1 and the c-Myc available from a TCGA database or an ENSEMBL database.

5. The method of claim 1, wherein the cancer comprises an 8q24.21 gain cancer.

6. The method of claim 1, wherein the cancer comprises medulloblastoma, breast cancer, ovarian cancer, lung cancer, prostate cancer, or a colorectal cancer.

7. The method of claim 1, wherein the siRNA comprises the nucleotide sequence set forth in SEQ ID NO. 3 and the nucleotide sequence set forth in SEQ ID NO. 4.

8. The method of claim 1, wherein the PVT1 splice variant CircPVT1 encodes a PEPc peptide comprising the sequence set forth in SEQ ID NO. 14.

* * * * *

46